(12) United States Patent
Yu et al.

(10) Patent No.: US 8,084,399 B2
(45) Date of Patent: Dec. 27, 2011

(54) PROCESS FOR SCREENING OF A BINDING AMPHIPHILIC PEPTIDES SPECIFIC FOR HAIRPIN RNA

(75) Inventors: Jaehoon Yu, Seoul (KR); Jeffrey Kieft, Denver, CO (US); Su Jin Lee, Seoul (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 12/540,246

(22) Filed: Aug. 12, 2009

(65) Prior Publication Data

US 2010/0173796 A1    Jul. 8, 2010

(30) Foreign Application Priority Data

Jan. 2, 2009    (KR) .................. 10-2009-0000147

(51) Int. Cl.
*C40B 30/04* (2006.01)
*A61K 38/00* (2006.01)

(52) U.S. Cl. .................. 506/9; 506/7; 506/18; 530/326; 536/23.1

(58) Field of Classification Search ................. 506/9, 7, 506/18; 530/326; 536/23.1
See application file for complete search history.

(56) References Cited

U.S. PATENT DOCUMENTS 6,358,921 B1 *  3/2002  Kondejewski et al. ........ 514/2.7
2008/0318797 A1 * 12/2008  Yu ...................................... 506/9

OTHER PUBLICATIONS

Lee, Su Jin; "An Approach to the Construction of Tailor-Made Amphiphilic Peptides That Strongly and Selectively Bind to Hairpin RNA Targets"; (2009) *J. Am. Chem. Soc.* 131(6):2224-2230.

* cited by examiner

*Primary Examiner* — T. D. Wessendrof
(74) *Attorney, Agent, or Firm* — Greenlee Sullivan P.C.

(57) ABSTRACT

The present invention relates to a screening method of an amphiphilic peptide specifically binding to hairpin RNA, more precisely a screening method of an amphiphilic peptide having specificity and strong binding strength to target hairpin RNA using peptide library comprising those peptides having modifications of both hydrophilic face and hydrophobic face. The method of the present invention provides a screening method of an amphiphilic peptide which is specific to hairpin RNA. So, the peptide selected by the method of the present invention can be effectively used for the study of hairpin RNA functions and for the production of a novel drug using an artificial peptide binding to a hairpin RNA target.

4 Claims, 5 Drawing Sheets

SEQUENCE LISTING

```
<160> NUMBER OF SEQ ID NOS: 41

<210> SEQ ID NO 1
<211> LENGTH: 16
<212> TYPE: PRT
<213> ORGANISM: Artificial Sequence
<220> FEATURE:
<223> OTHER INFORMATION: 1a synthetic peptide

<400> SEQUENCE: 1

Leu Lys Lys Leu Leu Lys Leu Leu Lys Lys Leu Leu Lys Leu Lys Gly
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: 1b synthetic peptide

<400> SEQUENCE: 2

Leu Ala Lys Leu Leu Lys Leu Leu Lys Lys Leu Leu Lys Leu Lys Gly
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: 1c synthetic peptide

<400> SEQUENCE: 3

Leu Lys Ala Leu Leu Lys Leu Leu Lys Lys Leu Leu Lys Leu Lys Gly
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: 1d synthetic peptide

<400> SEQUENCE: 4
```

-continued

Leu Lys Lys Leu Leu Ala Leu Lys Leu Leu Lys Leu Lys Gly
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: 1e synthetic peptide

<400> SEQUENCE: 5

Leu Lys Lys Leu Leu Lys Leu Leu Ala Lys Leu Leu Lys Leu Lys Gly
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: 1f synthetic peptide

<400> SEQUENCE: 6

Leu Lys Lys Leu Leu Lys Leu Leu Lys Ala Leu Leu Lys Leu Lys Gly
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: 1g synthetic peptide

<400> SEQUENCE: 7

Leu Lys Lys Leu Leu Lys Leu Leu Lys Lys Leu Leu Ala Leu Lys Gly
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: 1h synthetic peptide

<400> SEQUENCE: 8

Leu Lys Lys Leu Leu Lys Leu Leu Lys Lys Leu Leu Lys Leu Ala Gly
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: 2a synthetic peptide
<220> FEATURE:
<221> NAME/KEY: VARIANT
<222> LOCATION: (6)..(6)
<223> OTHER INFORMATION: Xaa is Orn

<400> SEQUENCE: 9

Leu Lys Lys Leu Leu Xaa Leu Leu Lys Lys Leu Leu Lys Leu Ala Gly
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: 2b synthetic peptide
<220> FEATURE:

```
<221> NAME/KEY: VARIANT
<222> LOCATION: (6)..(6)
<223> OTHER INFORMATION: Xaa is Dab

<400> SEQUENCE: 10

Leu Lys Lys Leu Leu Xaa Leu Leu Lys Lys Leu Leu Lys Leu Ala Gly
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: 2c synthetic peptide
<220> FEATURE:
<221> NAME/KEY: VARIANT
<222> LOCATION: (6)..(6)
<223> OTHER INFORMATION: Xaa is Dap

<400> SEQUENCE: 11

Leu Lys Lys Leu Leu Xaa Leu Leu Lys Lys Leu Leu Lys Leu Ala Gly
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: 2d synthetic peptide
<220> FEATURE:
<221> NAME/KEY: VARIANT
<222> LOCATION: (9)..(9)
<223> OTHER INFORMATION: Xaa is Orn

<400> SEQUENCE: 12

Leu Lys Lys Leu Leu Lys Leu Leu Xaa Lys Leu Leu Lys Leu Ala Gly
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: 2e synthetic peptide
<220> FEATURE:
<221> NAME/KEY: VARIANT
<222> LOCATION: (9)..(9)
<223> OTHER INFORMATION: Xaa is Dab

<400> SEQUENCE: 13

Leu Lys Lys Leu Leu Lys Leu Leu Xaa Lys Leu Leu Lys Leu Ala Gly
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: 2f synthetic peptide
<220> FEATURE:
<221> NAME/KEY: VARIANT
<222> LOCATION: (9)..(9)
<223> OTHER INFORMATION: Xaa is Dap

<400> SEQUENCE: 14

Leu Lys Lys Leu Leu Lys Leu Leu Xaa Lys Leu Leu Lys Leu Ala Gly
1               5                   10                  15

<210> SEQ ID NO 15
<211> LENGTH: 16
```

```
<212> TYPE: PRT
<213> ORGANISM: Artificial Sequence
<220> FEATURE:
<223> OTHER INFORMATION: 2g synthetic peptide
<220> FEATURE:
<221> NAME/KEY: VARIANT
<222> LOCATION: (13)..(13)
<223> OTHER INFORMATION: Xaa is Orn

<400> SEQUENCE: 15

Leu Lys Lys Leu Leu Lys Leu Leu Lys Lys Leu Leu Xaa Leu Ala Gly
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: 2h synthetic peptide
<220> FEATURE:
<221> NAME/KEY: VARIANT
<222> LOCATION: (13)..(13)
<223> OTHER INFORMATION: Xaa is Dab

<400> SEQUENCE: 16

Leu Lys Lys Leu Leu Lys Leu Leu Lys Lys Leu Leu Xaa Leu Ala Gly
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: 2i synthetic peptide
<220> FEATURE:
<221> NAME/KEY: VARIANT
<222> LOCATION: (13)..(13)
<223> OTHER INFORMATION: Xaa is Dap

<400> SEQUENCE: 17

Leu Lys Lys Leu Leu Lys Leu Leu Lys Lys Leu Leu Xaa Leu Ala Gly
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: 2j synthetic peptide
<220> FEATURE:
<221> NAME/KEY: VARIANT
<222> LOCATION: (6)..(6)
<223> OTHER INFORMATION: Xaa is Dab
<220> FEATURE:
<221> NAME/KEY: VARIANT
<222> LOCATION: (9)..(9)
<223> OTHER INFORMATION: Xaa is Orn

<400> SEQUENCE: 18

Leu Lys Lys Leu Leu Xaa Leu Leu Xaa Lys Leu Leu Lys Leu Ala Gly
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: 2k synthetic peptide
<220> FEATURE:
<221> NAME/KEY: VARIANT
<222> LOCATION: (9)..(9)
<223> OTHER INFORMATION: Xaa is Orn
```

```
<220> FEATURE:
<221> NAME/KEY: VARIANT
<222> LOCATION: (13)..(13)
<223> OTHER INFORMATION: Xaa is Dap

<400> SEQUENCE: 19

Leu Lys Lys Leu Leu Lys Leu Leu Xaa Lys Leu Leu Xaa Leu Ala Gly
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: 2l synthetic peptide
<220> FEATURE:
<221> NAME/KEY: VARIANT
<222> LOCATION: (6)..(6)
<223> OTHER INFORMATION: Xaa is Dab
<220> FEATURE:
<221> NAME/KEY: VARIANT
<222> LOCATION: (13)..(13)
<223> OTHER INFORMATION: Xaa is Dap

<400> SEQUENCE: 20

Leu Lys Lys Leu Leu Xaa Leu Leu Lys Lys Leu Leu Xaa Leu Ala Gly
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: 2m synthetic peptide
<220> FEATURE:
<221> NAME/KEY: VARIANT
<222> LOCATION: (6)..(6)
<223> OTHER INFORMATION: Xaa is Dab
<220> FEATURE:
<221> NAME/KEY: VARIANT
<222> LOCATION: (9)..(9)
<223> OTHER INFORMATION: Xaa is Orn
<220> FEATURE:
<221> NAME/KEY: VARIANT
<222> LOCATION: (13)..(13)
<223> OTHER INFORMATION: Xaa is Dap

<400> SEQUENCE: 21

Leu Lys Lys Leu Leu Xaa Leu Leu Xaa Lys Leu Leu Xaa Leu Ala Gly
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: 2n synthetic peptide

<400> SEQUENCE: 22

Trp Lys Lys Leu Leu Lys Leu Leu Lys Lys Leu Leu Lys Leu Ala Gly
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: 2o synthetic peptide

<400> SEQUENCE: 23

Leu Lys Lys Trp Leu Lys Leu Leu Lys Lys Leu Leu Lys Leu Ala Gly
```

```
                1               5                  10                 15

<210> SEQ ID NO 24
<211> LENGTH: 16
<212> TYPE: PRT
<213> ORGANISM: Artificial Sequence
<220> FEATURE:
<223> OTHER INFORMATION: 2p synthetic peptide

<400> SEQUENCE: 24

Leu Lys Lys Leu Trp Lys Leu Leu Lys Leu Leu Lys Leu Ala Gly
  1               5                  10                 15

<210> SEQ ID NO 25
<211> LENGTH: 16
<212> TYPE: PRT
<213> ORGANISM: Artificial Sequence
<220> FEATURE:
<223> OTHER INFORMATION: 2q synthetic peptide

<400> SEQUENCE: 25

Leu Lys Lys Leu Leu Lys Trp Leu Lys Leu Leu Lys Leu Ala Gly
  1               5                  10                 15

<210> SEQ ID NO 26
<211> LENGTH: 16
<212> TYPE: PRT
<213> ORGANISM: Artificial Sequence
<220> FEATURE:
<223> OTHER INFORMATION: 2r synthetic peptide

<400> SEQUENCE: 26

Leu Lys Lys Leu Leu Lys Leu Trp Lys Leu Leu Lys Leu Ala Gly
  1               5                  10                 15

<210> SEQ ID NO 27
<211> LENGTH: 16
<212> TYPE: PRT
<213> ORGANISM: Artificial Sequence
<220> FEATURE:
<223> OTHER INFORMATION: 2s synthetic peptide

<400> SEQUENCE: 27

Leu Lys Lys Leu Leu Lys Leu Leu Lys Lys Trp Leu Lys Leu Ala Gly
  1               5                  10                 15

<210> SEQ ID NO 28
<211> LENGTH: 16
<212> TYPE: PRT
<213> ORGANISM: Artificial Sequence
<220> FEATURE:
<223> OTHER INFORMATION: 2t synthetic peptide

<400> SEQUENCE: 28

Leu Lys Lys Leu Leu Lys Leu Leu Lys Leu Trp Lys Leu Ala Gly
  1               5                  10                 15

<210> SEQ ID NO 29
<211> LENGTH: 16
<212> TYPE: PRT
<213> ORGANISM: Artificial Sequence
<220> FEATURE:
<223> OTHER INFORMATION: 2u synthetic peptide

<400> SEQUENCE: 29

Leu Lys Lys Leu Leu Lys Leu Leu Lys Lys Leu Leu Lys Trp Ala Gly
  1               5                  10                 15
```

```
<210> SEQ ID NO 30
<211> LENGTH: 16
<212> TYPE: PRT
<213> ORGANISM: Artificial Sequence
<220> FEATURE:
<223> OTHER INFORMATION: 3a synthetic peptide
<220> FEATURE:
<221> NAME/KEY: VARIANT
<222> LOCATION: (6)..(6)
<223> OTHER INFORMATION: Xaa is Dab

<400> SEQUENCE: 30

Leu Lys Lys Leu Leu Xaa Trp Leu Lys Lys Leu Leu Lys Leu Ala Gly
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: 3b synthetic peptide
<220> FEATURE:
<221> NAME/KEY: VARIANT
<222> LOCATION: (9)..(9)
<223> OTHER INFORMATION: Xaa is Orn

<400> SEQUENCE: 31

Leu Lys Lys Leu Leu Lys Trp Leu Xaa Lys Leu Leu Lys Leu Ala Gly
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: 3c synthetic peptide
<220> FEATURE:
<221> NAME/KEY: VARIANT
<222> LOCATION: (13)..(13)
<223> OTHER INFORMATION: Xaa is Dap

<400> SEQUENCE: 32

Leu Lys Lys Leu Leu Lys Trp Leu Lys Lys Leu Leu Xaa Leu Ala Gly
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: 3d synthetic peptide
<220> FEATURE:
<221> NAME/KEY: VARIANT
<222> LOCATION: (9)..(9)
<223> OTHER INFORMATION: Xaa is Orn
<220> FEATURE:
<221> NAME/KEY: VARIANT
<222> LOCATION: (13)..(13)
<223> OTHER INFORMATION: Xaa is Dap

<400> SEQUENCE: 33

Leu Lys Lys Leu Leu Lys Trp Leu Xaa Lys Leu Leu Xaa Leu Ala Gly
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: 3e synthetic peptide
<220> FEATURE:
```

```
<221> NAME/KEY: VARIANT
<222> LOCATION: (6)..(6)
<223> OTHER INFORMATION: Xaa is Dab

<400> SEQUENCE: 34

Leu Lys Lys Leu Leu Xaa Leu Leu Lys Lys Leu Leu Lys Trp Ala Gly
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: 3f synthetic peptide
<220> FEATURE:
<221> NAME/KEY: VARIANT
<222> LOCATION: (9)..(9)
<223> OTHER INFORMATION: Xaa is Orn

<400> SEQUENCE: 35

Leu Lys Lys Leu Leu Lys Leu Leu Xaa Lys Leu Leu Lys Trp Ala Gly
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: 3g synthetic peptide
<220> FEATURE:
<221> NAME/KEY: VARIANT
<222> LOCATION: (13)..(13)
<223> OTHER INFORMATION: Xaa is Dap

<400> SEQUENCE: 36

Leu Lys Lys Leu Leu Lys Leu Leu Lys Lys Leu Leu Xaa Trp Ala Gly
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: 3h synthetic peptide
<220> FEATURE:
<221> NAME/KEY: VARIANT
<222> LOCATION: (9)..(9)
<223> OTHER INFORMATION: Xaa is Orn
<220> FEATURE:
<221> NAME/KEY: VARIANT
<222> LOCATION: (13)..(13)
<223> OTHER INFORMATION: Xaa is Dap

<400> SEQUENCE: 37

Leu Lys Lys Leu Leu Lys Leu Leu Xaa Lys Leu Leu Xaa Trp Ala Gly
1               5                   10                  15

<210> SEQ ID NO 38
<211> LENGTH: 50
<212> TYPE: DNA
<213> ORGANISM: Artificial Sequence
<220> FEATURE:
<223> OTHER INFORMATION: RRE template sequence
<220> FEATURE:
<221> NAME/KEY: conflict
<222> LOCATION: (1)..(20)
<223> OTHER INFORMATION: promoter

<400> SEQUENCE: 38
ccgtaatacg actcactata ggtgggcgca gcttcggctg acggtacacc           50
```

```
<210> SEQ ID NO 39
<211> LENGTH: 51
<212> TYPE: DNA
<213> ORGANISM: Artificial Sequence
<220> FEATURE:
<223> OTHER INFORMATION: TAR template sequence
<220> FEATURE:
<221> NAME/KEY: conflict
<222> LOCATION: (1)..(20)
<223> OTHER INFORMATION: promoter

<400> SEQUENCE: 39
ccgtaatacg actcactata ggccagatct gagcctggga gctctctggc c        51

<210> SEQ ID NO 40
<211> LENGTH: 47
<212> TYPE: DNA
<213> ORGANISM: Artificial Sequence
<220> FEATURE:
<223> OTHER INFORMATION: 16S template sequence
<220> FEATURE:
<221> NAME/KEY: conflict
<222> LOCATION: (1)..(18)
<223> OTHER INFORMATION: promoter

<400> SEQUENCE: 40
ccgtaatacg actcactata ggcgtcacac cttcgggtga agtcgcc              47

<210> SEQ ID NO 41
<211> LENGTH: 48
<212> TYPE: DNA
<213> ORGANISM: Artificial Sequence
<220> FEATURE:
<223> OTHER INFORMATION: IRES template sequence
<220> FEATURE:
<221> NAME/KEY: conflict
<222> LOCATION: (1)..(20)
<223> OTHER INFORMATION: promoter

<400> SEQUENCE: 41
ccgtaatacg actcactata gggaccgtgc atcatgagca caaatccc             48
```

PROCESS FOR SCREENING OF A BINDING AMPHIPHILIC PEPTIDES SPECIFIC FOR HAIRPIN RNA

CROSS-REFERENCE TO RELATED APPLICATIONS

This application claims priority under 35 USC 119(a)-(d) to Korea Application No. 10-2009-0000147 filed on Jan. 2, 2009, the contents of which are hereby incorporated by reference in their entirety.

BACKGROUND OF THE INVENTION

1. Field of the Invention

The present invention relates to screening methods for amphiphilic peptides binding specifically to hairpin RNA, more precisely to screening methods for amphiphilic peptides having target hairpin RNA specificity and powerful binding force as well by using peptide libraries in which the hydrophilic face and hydrophobic face of the amphiphilic peptide are changed.

2. Description of the Related Art

RNA hairpins share similarities in morphology and play a very important role in gene expression, etc, from prokaryotes to eukaryotes. Therefore, such RNA molecules can be targets for drugs. In particular, hairpin RNAs have deep grooves similar to DNA, to which low molecular substances can be conjugated. There are many RNA binding low-molecular compounds but their binding force and specificity have been always in question.

Peptides are believed to be a promising alternative for such low-molecular substances, which is supported by the identification of Rev peptide having strong binding force and specificity to natural hairpin RNA. The present inventors also confirmed previously that an amphiphilic peptide having alpha-helix structure could bind specifically to hairpin RNA. There are some other natural peptides specific to hairpin RNA; however, a method to produce ligands specific to hairpin RNA by using such alpha-helical peptides has not been established. Encouraged by the activity of natural peptides, amphiphilic peptides composed of leucine and lysine have been prepared.

It is difficult to distinguish target hairpin RNA molecules because of their high similarity. In addition, hairpin RNA has a more promiscuous structure than other RNAs. Accordingly, it is very difficult to prepare a ligand specific to non-selective hairpin molecules without preparatory study. Recent techniques cannot even distinguish hairpin molecules having promiscuous structure from that with simple structure.

Amphiphilic peptides generally conjugate well to hairpins. When slightly modified but non-narrowed peptides were conjugated to various hairpins, the binding force was not much different from that to hairpin of wide-open structures. But, some specific hairpins are presumed to be useful to separate non-narrowed peptides. So it is believed alanine-scanned peptide libraries might be a help to judge the complexity of the target hairpin.

The present inventors synthesized an amphiphilic peptide binding to hairpin RNA whose hydrophilic face and hydrophobic face are modified and further completed this invention by establishing a method for screening the amphiphilic peptide which has better specificity to hairpin RNA and stronger binding force as well than the natural amphiphilic peptide.

SUMMARY OF THE INVENTION

It is an object of the present invention to provide a method for judging complexity of hairpin RNA using artificially prepared amphiphilic peptides and a method for screening amphiphilic peptides having specificity to target hairpin RNA and strong binding force as well.

To achieve the above object, the present invention provides an amphiphilic peptide library containing one or more amphiphilic peptides which have the amino acid sequences arranged with the hydrophobic amino acid leucine (L) and the hydrophilic amino acid lysine (K) or glycine (G) alternately by ones or twos where one lysine (K) is substituted with alanine (A).

The present invention also provides a method of screening hairpin RNA with promiscuous structure comprising the following steps:

1) constructing an amphiphilic peptide library;
2) synthesizing the target hairpin RNA on the amphiphilic peptide library;
3) calculating the amphiphilic peptide specific binding force of RNA and binding deviation by measuring fluorescent anisotropy of the mixture composed of the amphiphilic peptide, hairpin RNA and a probe by using fluoro spectrophotometer; and
4) selecting hairpin RNA having weak amphiphilic peptide specific binding force and small binding deviation.

The present invention also provides an amphiphilic peptide library containing one or more amphiphilic peptides which have the amino acid sequences arranged with the hydrophobic amino acid leucine (L) and the hydrophilic amino acid lysine (K) or glycine (G) alternately by ones or twos where one or two lysines (K) are substituted with other amino acids having less carbon number.

The present invention also provides an amphiphilic peptide library containing one or more amphiphilic alpha-helical peptides which have the amino acid sequences arranged with the hydrophobic amino acid leucine (L) and the hydrophilic amino acid lysine (K) or glycine (G) alternately by ones or twos where at least one leucine (L) is substituted with tryptophan (W).

The present invention also provides an amphiphilic peptide library containing one or more amphiphilic peptides which have the amino acid sequences arranged with the hydrophobic amino acid leucine (L) and the hydrophilic amino acid lysine (K) or glycine (G) alternately by ones or twos where one or two lysines (K) are substituted with other amino acids having less carbon number and one leucine (L) is substituted with tryptophan (W).

The present invention also provides a screening method using an amphiphilic peptide binding specifically to target hairpin RNA comprising the following steps:

1) constructing an amphiphilic peptide library;
2) synthesizing the target hairpin RNA for screening of specific ligands;
3) calculating binding force between RNA and the amphiphilic peptide by measuring fluorescent anisotropy of the mixture composed of the amphiphilic peptide, hairpin RNA and probe by using fluoro spectrophotometer; and
4) selecting the amphiphilic peptide demonstrating strong binding force to target hairpin RNA.

The present invention further provides a use of the amphiphilic peptide selected by the screening method for the production of a RNA activity inhibitor having hairpin structure.

The present invention also provides a use of the amphiphilic peptide selected by the screening method for the production of a therapeutic agent or a diagnostic reagent for AIDS when the target hairpin RNA is RRE RNA or TAR RNA.

The present invention also provides a use of the amphiphilic peptide selected by the screening method for the production of an antibiotic or a diagnostic reagent when the target hairpin RNA is 16S rRNA-A-site.

In addition, the present invention provides a use of the amphiphilic peptide selected by the screening method for the production of a therapeutic agent or a diagnostic reagent for hepatitis C when the target hairpin RNA is IRES RNA.

Terms and definitions used in this description are described hereinafter.

In this invention, the term 'alanine scanning' indicates the technique to substitute amino acids with (methyl)alanine having no functional groups in order to search important functional groups.

In this invention, the terms 'promiscuous' and 'promiscuous structure' indicate that a target binds to any ligand or multiple ligands regardless of the types of the ligand.

In this invention, the term 'specific' indicates the opposite meaning of 'promiscuous' which means it is binding to only a specific ligand.

BRIEF DESCRIPTION OF THE DRAWINGS

The application of the preferred embodiments of the present invention is best understood with reference to the accompanying drawings.

DETAILED DESCRIPTION OF THE INVENTION

Figure 1:
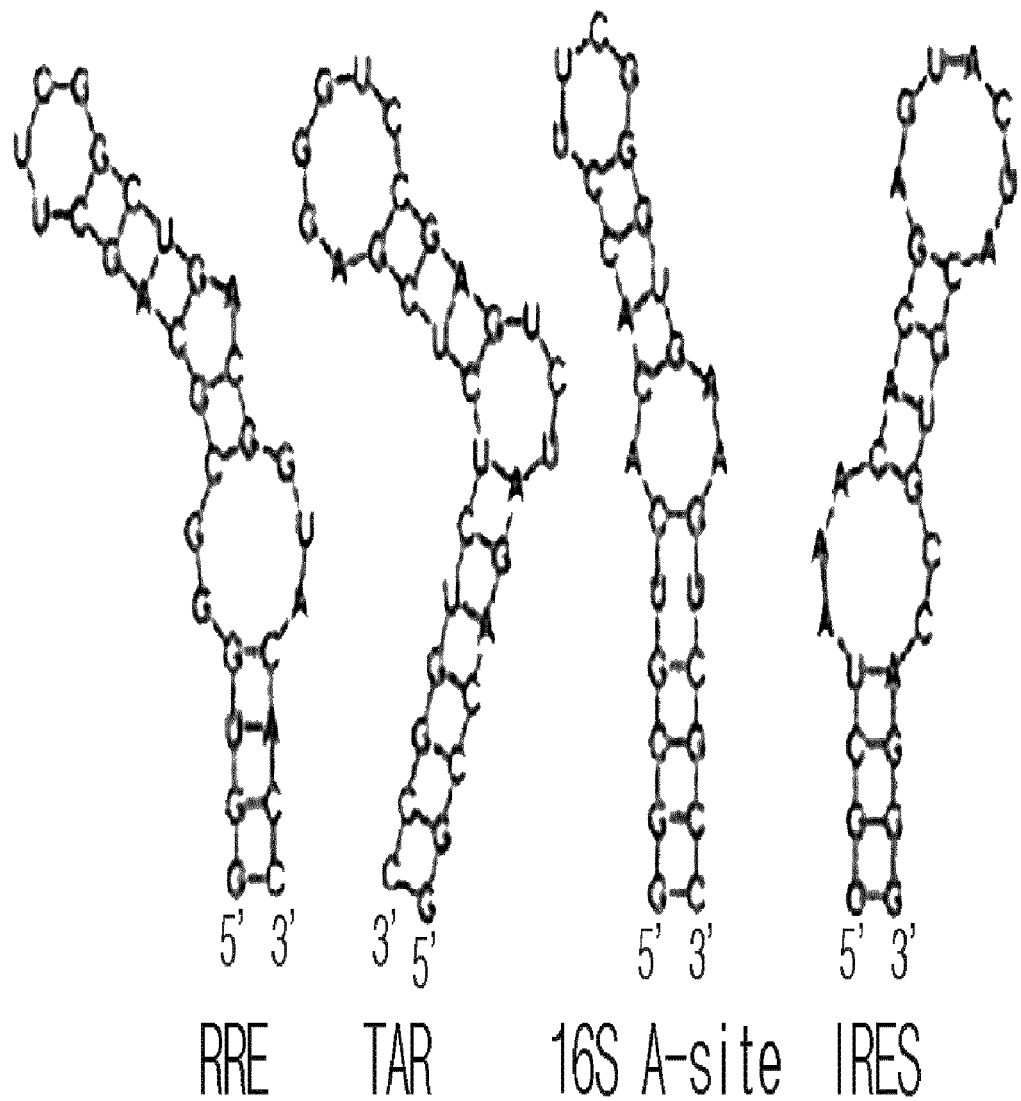
FIG. 1 is a diagram illustrating the secondary structure of the hairpin RNA used in this invention.

Hereinafter, the present invention is described in detail.

The present invention provides an amphiphilic peptide library containing one or more amphiphilic peptides which have the amino acid sequences arranged with the hydrophobic amino acid leucine (L) and the hydrophilic amino acid lysine (K) or glycine (G) alternately by ones or twos where one lysine (K) is substituted with alanine (A).

The amphiphilic peptide has preferably one or more peptides having one or more of the amino acid sequences represented by SEQ. ID. NO: 2-NO: 8, but not always limited thereto.

The amphiphilic peptide is preferably composed of 14-150 amino acids to have stable secondary structure, but not always limited thereto.

The present invention also provides a method of screening promiscuous hairpin RNA comprising the following steps:

1) constructing an amphiphilic peptide library containing one or more amphiphilic peptides which have the amino acid sequences arranged with the hydrophobic amino acid leucine (L) and the hydrophilic amino acid lysine (K) or glycine (G) alternately by ones or twos where one lysine (K) is substituted with alanine (A);

2) synthesizing the target hairpin RNA on the amphiphilic peptide library;

3) calculating amphiphilic peptide specific binding force of RNA and binding deviation by measuring fluorescent anisotropy of the mixture composed of the amphiphilic peptide, hairpin RNA and probe by using fluoro spectrophotometer; and 4) selecting promiscuous hairpin RNA having weak amphiphilic peptide specific binding force and small binding deviation.

In this invention, the alanine scanned peptide library was first prepared and the binding force of the amphiphilic peptide to each IRES, RRE, TAR and 16S A-site hairpin RNA and alpha-helical structure thereof was measured (see Table 1, Table 2 and Table 3).

As a result, the binding force of the amphiphilic peptide to TAR was determined to be the weakest and the standard deviation was also the smallest. On the contrary, binding force to 16S A-site was the strongest, while binding force to IRES showed the biggest standard deviation. These results suggest that the TAR hairpin has the highest morphological flexibility so that it can fit various amphiphilic peptides.

Among 7 promiscuous peptides, 4 peptides demonstrated higher binding force to TAR than original peptides, while only one peptide among those 7 peptides demonstrated higher binding force to IRES. This means that IRES can be a more specific hairpin target. The difference of binding force to IRES of those 7 promiscuous peptides was bigger, which is believed to be because of the characteristics of IRES. The amine group which plays a very important role in the interaction between the IRES hairpin and the peptide is located at the sites of #6, #9 and #13. When the amine group is eliminated, binding force is significantly decreased. Therefore, it can be judged whether a specific hairpin is promiscuous or not by investigating RNA hairpin specific binding force and binding deviation by using alpha scanning peptide libraries.

Only one peptide demonstrated reduced binding force to TAR, while at least three peptides showed reduced binding force to IRES. This result indicates that at least three specific lysines are essential for the interaction between the peptide and IRES. But, any lysine will do to bind to TAR, which can be a typical characteristic of the promiscuous target hairpin. Therefore, it can be judged what lysine residue plays a crucial role in binding with target hairpin RNA by using alpha scanning peptide libraries.

The present invention also provides an amphiphilic peptide library containing one or more amphiphilic peptides which have the amino acid sequences arranged with the hydrophobic amino acid leucine (L) and the hydrophilic amino acid lysine (K) or glycine (G) alternately by ones or twos where one or two lysines (K) are substituted with other amino acids having less carbon number.

The amino acid having less carbon number than lysine is preferably selected from the group consisting of ornithine (Orn), 1,4-diaminobutyric acid (Dab) and 1,3-dipropanoic acid (Dap), but not always limited thereto.

The said amphiphilic peptide preferably contains one or more peptides having one or more of the amino acid sequences represented by SEQ. ID. NO: 9-NO: 21, but not always limited thereto.

The amphiphilic peptide is preferably composed of 14-150 amino acids to have stable secondary structure, but not always limited thereto.

In this invention, the second generation peptides were prepared by substituting lysines at #6, #9 and #13, recognized as important amine groups by alanine scanning, with ornithine (Orn), 1,4-diaminobutyric acid (Dab) or 1,3-dipropanoic acid (Dap) having less carbon number than lysine, by which binding force of the amphiphilic peptide to each IRES, RRE, TAR and 16S A-site hairpin RNA and alpha-helical structures thereof were examined. When such amino acids having amine groups linked to shorter residues are used, the outer diameter of the peptide becomes shorter, suggesting that the peptide can be positioned deep in the target RNA groove. In addition, the important amine group remains allowing Van der Waals forces to work more strongly and allowing interaction between the peptide of hydrophobic face and the target RNA to be recognized (see Table 1, Table 2 and Table 4).

As a result, binding force to IRES of the second generation peptides prepare by using short amino acid was significantly increased, compared with that of the first generation peptides. Maximum points were also observed by the decrease of the carbon number, and at last three times higher binding force was observed, compared with when lysine was used instead of the short amino acid. The peptide in which at least two lysines were substituted with short amino acids demonstrated significantly increased binding force, compared with the peptide having the substitution of only one peptide. Accordingly, these second generation peptides have much improved selectivity, compared with most other peptides.

The present invention also provides an amphiphilic peptide library containing one or more amphiphilic alpha-helical peptides which have the amino acid sequences arranged with the hydrophobic amino acid leucine (L) and the hydrophilic amino acid lysine (K) or glycine (G) alternately by ones or twos where one leucine (L) is substituted with tryptophan (W).

The said amphiphilic peptide preferably has one or more peptides having one or more of the amino acid sequences represented by SEQ. ID. NO: 22-NO: 29, but not always limited thereto.

The amphiphilic peptide is preferably composed of 14-150 amino acids to have stable secondary structure, but not always limited thereto.

The amphiphilic peptide library herein preferably contains one or more amphiphilic peptides which have the amino acid sequences arranged with the hydrophobic amino acid leucine (L) and the hydrophilic amino acid lysine (K) or glycine (G) alternately by ones or twos where one or two lysines (K) are substituted with other amino acids having less carbon number and one leucine (L) is substituted with tryptophan (W), but not always limited thereto.

In this invention, the hydrophobic part of the amphiphilic peptide can also be a part of improving binding force because it can be bound to the RNA when the peptide is located deep within the target RNA groove. It was confirmed that the amphiphilic peptide having modified hydrophobic region had increased binding force to IRES. It has been known that recognition of aliphatic amino acids and RNA does not significantly differ and that aromatic amino acids might have different recognition characteristics. So, the tryptophan scanning peptide library was constructed by inserting tryptophan in 8 leucine sites on the hydrophobic face, followed by investigation of binding force to IRES (see Table 1, Table 2, and Table 5).

As a result, binding force of the tryptophan scanned peptide to IRES was four fold higher than that of the original amphiphilic peptide, suggesting the hydrophobic face can recognize RNA. This tryptophan effect was site specific. Because of tryptophan, some of the specific peptides demonstrated increased alpha-helix and thereby increased binding force. However, some of those peptides maintained their alpha-helix without being increased but the binding force to IRES was significantly increased. That was because the indole group of tryptophan could increase recognition mediated by RNA specific nucleotide sequence and specific arrangement. Even if the tryptophan scanned peptide was a promiscuous peptide, some specific tryptophan scanned peptides had high binding force to IRES hairpin, suggesting that there is a specific recognition between indole and RNA bases.

The present invention also provides an amphiphilic peptide library containing one or more amphiphilic peptides which have the amino acid sequences arranged with the hydrophobic amino acid leucine (L) and the hydrophilic amino acid lysine (K) or glycine (G) alternately by ones or twos where one or two lysines (K) are substituted with other amino acids having less carbon number and one leucine (L) is substituted with tryptophan (W).

The amino acid having less carbon number than lysine is preferably selected from the group consisting of ornithine (Orn), 1,4-diaminobutyric acid (Dab) and 1,3-dipropanoic acid (Dap), but not always limited thereto.

The said amphiphilic peptide preferably contains one or more peptides having one or more of the amino acid sequences represented by SEQ. ID. NO: 30-NO: 37, but not always limited thereto.

The amphiphilic peptide is preferably composed of 14-150 amino acids to have stable secondary structure, but not always limited thereto.

In this invention, to confirm whether the change of both the hydrophilic face and hydrophobic face can be equally effective at the same time, a third generation peptide library prepared by the combination of those having changes on both the hydrophilic face and hydrophobic face was synthesized. Then, the binding force to IRES hairpin was measured (see Table 1, Table 2 and Table 6).

As a result, most of the third generation peptides did not meet the expectation of high binding capacity, but binding forces varied. Only a few peptides of those third generation peptides demonstrated high binding force to IRES hairpin, suggesting that the changes on both faces could be dependent to each other and thus the optimum effect could be expected when they were complementary. Fluorescent strength varied from the types of peptides and the location of tryptophan. So, the indole group of tryptophan recognized a specific nucleotide of IRES. In conclusion, simultaneous changes on both hydrophilic face and hydrophobic face could increase binding force to a specific hairpin as high as 80 times, and a peptide having at least 50 times higher specificity could be obtained.

The present invention also provides a method of screening an amphiphilic peptide binding specifically to target hairpin RNA comprising the following steps:

1) constructing the said amphiphilic peptide library;
2) synthesizing the target hairpin RNA for screening of the specific ligand;
3) calculating binding force between RNA and the amphiphilic peptide by measuring fluorescent anisotropy of the mixture composed of the amphiphilic peptide, hairpin RNA and probe by using fluoro spectrophotometer; and
4) selecting the amphiphilic peptide demonstrating strong binding force to target hairpin RNA.

In this method, the hairpin RNA of step 2) is preferably selected from the group consisting of RRE (Rev responsive element) RNA, TAR (trans-activating region) RNA, A-site of 16S rRNA and IRES (Internal Ribosome Entry Site) RNA, and is more preferably IRES RNA, but not always limited thereto.

In this method, the probe of step 3) is preferably a compound which is fluorescent and labeled with a tag capable of competing with the amphiphilic peptide for binding to target hairpin RNA, which is preferably rhodamine conjugated rev peptide (Rev-N-rhodamine), but not always limited thereto.

In this invention, the ligand selectively binding to hairpin RNA was produced by using the amphiphilic peptide library. First, amino acids having a lower carbon number than lysine were used in order to locate a peptide deep in RNA groove to help hydrophobic face highly recognize other regions of RNA. Second, leucine in the amphiphilic peptide was substituted with tryptophan having and indole group, resulting in the increase of recognition of hydrophobic region so as to provide a tryptophan site specific effect. Third, a synergy effect was brought by combining the above two strategies. That is, the ligand peptide having target RNA specificity and strong RNA binding force was produced by changing both sides of the amphiphilic peptide.

The present invention further provides a use of the amphiphilic peptide selected by the screening method for the production of a RNA activity inhibitor having hairpin structure.

The present invention also provides a use of the amphiphilic peptide selected by the screening method for the production of a therapeutic agent or a diagnostic reagent for AIDS when the target hairpin RNA is RRE RNA or TAR RNA.

The present invention also provides a use of the amphiphilic peptide selected by the screening method for the production of an antibiotic or a diagnostic reagent when the target hairpin RNA is 16S rRNA-A-site.

In addition, the present invention provides a use of the amphiphilic peptide selected by the screening method for the production of a therapeutic agent or a diagnostic reagent for hepatitis C when the target hairpin RNA is IRES RNA.

RNA structure is not as complicated or varied as that of proteins. So, it is easily distinguished by various compounds. To develop a novel drug targeting RNA, a target RNA specific peptide has to be first selected. To do so, various peptides are prepared by modifying a peptide and then screening the prepared peptides that are highly specific to the target RNA, resulting in a target specific peptide. Then, a RNA specific ligand can be prepared.

Once an amphiphilic peptide turns into a hairpin RNA specific ligand, it is also possible to make more changes in the amphiphilic peptide to have more specificity. A peptide having alpha-helical structure can fit more deeply in the groove of a specific hairpin structure, suggesting that both hydrophilic face and hydrophobic face of the amphiphilic peptide can be complementarily bound to RNA. Therefore, a target hairpin RNA specific peptide can be prepared by changing both sides of the amphiphilic peptide. That is, by changing the hydrophilic face of the amphiphilic peptide, changing the hydrophobic face of the peptide or changing both sides of the peptide results in the increase of binding force to specific hairpin RNA at least 80 times as high as the original peptide or specificity at least 50 times as high as the original peptide.

A target hairpin RNA ligand can be prepared by the processes of constructing various peptide libraries; and selecting target hairpin RNA specific amphiphilic peptides.

The RNA+ligand is target hairpin RNA specific and has a binding force strong enough to inhibit target hairpin RNA activity, so that it can be effectively used as a target hairpin RNA activity inhibitor. When the target hairpin RNA is RRE hairpin RNA and TAR hairpin RNA that can be a target of HIV, or 16S ribosomal RNA A-site, or IRES domain IV hairpin that can be a target of HCV, their specific RNA ligands can be effectively used for the preparation of drugs or diagnostic reagents targeting HIV, 16S A-site or HCV.

ADVANTAGEOUS EFFECTS

The present invention provides a method of screening RNA specific peptides using an amphiphilic peptide. According to this method, an amphiphilic peptide which is hairpin RNA specific and has strong binding force is selected. The selected peptide can also be used for the study of hairpin RNA functions. In addition, the peptide binds to target hairpin RNA stronger and more specifically than natural peptides. So, this artificial peptide can be effectively used for the production of novel drugs.

Practical and presently preferred embodiments of the present invention are illustrative as shown in the following Examples, Experimental Examples and Manufacturing Examples. However, it will be appreciated that those skilled in the art, on consideration of this disclosure, may make modifications and improvements within the spirit and scope of the present invention.

Example 1

Synthesis of Peptide Library

<1-1> Synthesis of Peptide

Peptide synthesis was performed by well-infirmed Fmoc solid phase peptide synthesis method. 100 mg (0.064 mmol) of Rink Amide resin (Novabiochem) was placed in a vessel, to which 1 ml of methylene chloride was added to inflate thereof. The mixture was inflated by adding 1 ml of DMF (dimethylformamide) for 5 minutes. Deprotection of the resin was performed using 1 ml of 20% piperidine (in DMF) for 5 minutes (three times), followed by washing with 1 ml of DMF five times. Six equivalents of the Fmoc-deprotected amino acid was reacted with a solution containing six equivalents (198 mg) of each PyBop [(benzotriazol-1-yloxy)tripyrrolidinophosphonium hexafluorophosphate] and DIPEA (diisopropylethylamine) for at least 60 minutes. Upon completion of the reaction, the reactant was washed with 1 ml of DMF three times. TNBS test was performed to confirm whether the reaction was successfully done. Particularly, one drop of 10% DIPEA dissolved in DMF and one drop of 2,4,6-trinitrobenzenesulfonic acid (TNBS) dissolved in DMF were dropped on the sample. When it was colorless, it meant reaction was completed. Once amide binding was completed, Fmoc-amino acids having designed sequence were used stepwise 16 times. As a result, 16-mer peptide was synthesized. After finishing the last coupling, the resin was washed with 1 ml of DMF and 1 ml of methanol three times each, followed by vacuum-drying. Two hundred mg of the resin containing the peptide synthesized by the solid phase peptide synthesis method was loaded in 5 ml of cleavage solution [2.5% TIS (triisopropylsilane), 2.5% water, 95% TFA (trifluoroacetic acid)], followed by stirring for 2 hours. As a result, the synthesized peptide was separated from the resin.

The resin was filtered and excessive TFA was eliminated by using nitrogen. 50 ml of n-hexane:diethyl ether (V:V=1:1) solution cooled at 0° C. in advance was added thereto to elute the synthesized peptide.

<1-2> Purification of Peptide

The eluted peptide was dissolved in dimethyl sulfoxide, followed by purification by HPLC using C18 column. 0.1% TFA added water and acetonitrile were used as HPLC solvents. Particularly, crude peptide was dissolved in dimethyl sulfoxide at the concentration of 10 mg/ml. 100 μl of the solution was loaded in HPLC, followed by purification of the peptide with changing the composition of the solvent from 10% acetonitrile to 45% acetonitrile for 40 minutes. At that time, flow rate was 3 ml/min and detection wavelength was 220 nm. The peptide was recovered at the time point of 20-30 minutes, and vacuumed to evaporate acetonitrile, followed by freeze-drying. The purified acridine-alpha-helical peptide complex was identified by measuring the molecular weight using MOLDI-TOF mass spectrometry.

TABLE 1

Results of mass spectrometry with the synthesized peptide

| No. | Sequence (SEQ. ID. NO:) | Mass (M + H⁺) Calculated value | Mass (M + H⁺) Measured value |
|---|---|---|---|
| 1a | LKKLLKLLKKLLKLKG (SEQ. ID. NO: 1) | 1876.6 | 1877.2 |
| Rev-N-rhodamine | | 3260.8 | 3260.7 |
| 1b | LAKLLKLLKKLLKLKG (SEQ. ID. NO: 2) | 1819.3 | 1819.0 |
| 1c | LKALLKLLKKLLKLKG (SEQ. ID. NO: 3) | 1819.3 | 1819.0 |
| 1d | LKKLLALLKKLLKLKG (SEQ. ID. NO: 4) | 1819.3 | 1819.3 |
| 1e | LKKLLKLLAKLLKLKG (SEQ. ID. NO: 5) | 1819.3 | 1819.1 |
| 1f | LKKLLKLLKALLKLKG (SEQ. ID. NO: 6) | 1819.3 | 1819.2 |
| 1g | LKKLLKLLKKLLALKG (SEQ. ID. NO: 7) | 1819.3 | 1819.1 |
| 1h | LKKLLKLLKKLLKLAG (SEQ. ID. NO: 8) | 1819.3 | 1819.1 |
| 2a | LKKLLOrnLLKKLLKLAG (SEQ. ID. NO: 9) | 1847.3 | 1847.0 |
| 2b | LKKLLDabLLKKLLKLAG (SEQ. ID. NO: 10) | 1833.3 | 1833.4 |
| 2c | LKKLLDapLLKKLLKLAG (SEQ. ID. NO: 11) | 1819.3 | 1819.4 |
| 2d | LKKLLKLLOrnKLLKLAG (SEQ. ID. NO: 12) | 1847.3 | 1847.5 |
| 2e | LKKLLKLLDabKLLKLAG (SEQ. ID. NO: 13) | 1833.3 | 1833.8 |
| 2f | LKKLLKLLDapKLLKLAG (SEQ. ID. NO: 14) | 1819.3 | 1820.3 |
| 2g | LKKLLKLLKKLLOrnLAG (SEQ. ID. NO: 15) | 1847.3 | 1847.5 |
| 2h | LKKLLKLLKKLLDabLAG (SEQ. ID. NO: 16) | 1833.3 | 1833.4 |
| 2i | LKKLLKLLKKLLDapLAG (SEQ. ID. NO: 17) | 1819.3 | 1819.4 |
| 2j | LKKLLDabLLOrnKLLKLAG (SEQ. ID. NO: 18) | 1819.3 | 1820.0 |
| 2k | LKKLLKLLOrnKLLDapLAG (SEQ. ID. NO: 19) | 1805.3 | 1805.4 |
| 2l | LKKLLDabLLKKLLDapLAG (SEQ. ID. NO: 20) | 1791.3 | 1791.3 |
| 2m | LKKLLDabLLOrnKLLDapLAG (SEQ. ID NO: 21) | 1777.2 | 1777.6 |
| 2n | WKKLLKLLKKLLKLAG (SEQ. ID. NO: 22) | 1934.3 | 1934.3 |
| 2o | LKKWLKLLKKLLKLAG (SEQ. ID. NO: 23) | 1934.3 | 1934.4 |
| 2p | LKKLWKLLKKLLKLAG (SEQ. ID. NO: 24) | 1934.3 | 1934.4 |
| 2q | LKKLLKWLKKLLKLAG (SEQ. ID. NO: 25) | 1934.3 | 1934.3 |
| 2r | LKKLLKLWKKLLKLAG (SEQ. ID. NO: 26) | 1934.3 | 1934.5 |
| 2s | LKKLLKLLKKWLKLAG (SEQ. ID. NO: 27) | 1934.3 | 1934.6 |
| 2t | LKKLLKLLKKLWKLAG (SEQ. ID. NO: 28) | 1934.3 | 1934.1 |
| 2u | LKKLLKLLKKLLKWAG (SEQ. ID. NO: 29) | 1934.3 | 1934.1 |
| 3a | LKKLLDabWLKKLLKLAG (SEQ. ID. NO: 30) | 1906.3 | 1906.4 |
| 3b | LKKLLKWLOrnKLLKLAG (SEQ. ID. NO: 31) | 1920.3 | 1920.4 |
| 3c | LKKLLKWLKKLLDapLAG (SEQ. ID. NO: 32) | 1892.3 | 1892.4 |
| 3d | LKKLLKWLOrnKLLDapLAG (SEQ. ID. NO: 33) | 1878.3 | 1878.3 |
| 3e | LKKLLDabLLKKLLKWAG (SEQ. ID. NO: 34) | 1906.3 | 1906.6 |
| 3f | LKKLLKLLOrnKLLKWAG (SEQ. ID. NO: 35) | 1920.3 | 1920.5 |
| 3g | LKKLLKLLKKLLDapWAG (SEQ. ID. NO: 36) | 1892.3 | 1892.8 |
| 3h | LKKLLKLLOrnKLLDapWAG (SEQ. ID. NO: 37) | 1878.3 | 1878.3 |

Example 2

Preparation of Target RNA

RNA transcription was performed in vitro using DNA as a template with T7 RNA polymerase, and then a series of separation procedure followed. DNA templates and promoter regions (underlined parts) are as follows: RRE template sequence: 5'-

CCGTAATACGACTCACTATAGGTGGGCGCAGCT TCGGCTGACGGTACACC-3' (SEQ. ID. NO: 42), TAR template sequence: 5'-CCGTAATACGACTCACTATAGGCCAGATCTGAG CCTGGGAGCTCTCTGGCC-3' (SEQ. ID. NO: 43), 16S template sequence: 5'-CCGTAATACGACTCACTATAGGCGTCACACCTTC GGGTGAAGTCGCC-3' (SEQ. ID. NO: 44), IRES template sequence: 5'-CCGTAATACGACTCACTATAGGGACCGTGCATCA TGAGCACAAATCCC-3' (SEQ. ID. NO: 45). Selected four hairpin RNAs were RRE hairpin RNA and TAR hairpin RNA (referred as 'RRE and 'TAR') that can be a target of HIV, 16S ribosomal RNA A-site (referred as '16S A-site' hereinafter), and IRES domain IV hairpin (referred as 'IRES' hereinafter) that can be a target of HCV. Each template DNA of IRES, RRE, TAR and 16S A-site was purchased from Sigma-Aldrich, transcribed, and separated by a series of reactions. The sequences of the template DNAs are shown in Table 2.

Particularly, to change T7 promoter linked single-stranded template DNA into double-stranded DNA, 100 pmol of each sense DNA strand and antisense DNA strand were mixed, followed by reaction at 95° C. for 5 minutes. The mixture was cooled down slowly at room temperature. For transcription, 100 pmol of double-stranded DNA, 20 µl of 5× buffer (200 mM Tris-Cl, (pH7.5), 10 mM spermidin, 30 mM MgCl2, 25 mM NaCl), 10 µl of 100 mM DTT (dithiothreitol), 20 µl of 2.5 mM NTP (ribonucleoside triphosphate) mix and 5 µl of T7 RNA polymerase were used. The mixture was reacted at 37° C. for 4 hours, then 1 µl of RQ1 RNase-free DNase (1 unit/µl) (PROMEGA, USA) was added thereto, followed by reaction for one hour under the same conditions as the above. Protein was removed by using the equal amount of phenol mixture (Phenol:Chloroform:Isoamyl alcohol=25:24:1), followed by precipitation using ethanol at −70° C. for 1 hour. The reactant was loaded on 15% denaturation PAGE gel containing 7 M UREA. Bands exactly in the size of 30-mer were cut out and placed in an eppendorf tube containing 500 µl of elution buffer (0.5 M ammonium acetate, 1 mM EDTA, 0.2% SDS, pH 8.0), which stood at 37° C. for 4 hours. Only the solution was transferred into a new eppendorf tube, followed by phenol extraction by the same manner as described above. The solution containing RNA was precipitated using ethanol again and the obtained RNA was quantified by UV.

TABLE 2

DNA templates used for RNA synthesis

| RNA | DNA template | SEQ. ID. NO: |
|-----|-------------|--------------|
| RRE | 5'-CCGTAATACGACTCACTATAGGTGGG CGCAGCTTCGGCTGACGGTACACC-3' | SEQ. ID. NO: 38 |
| TAR | 5'-CCGTAATACGACTCACTATAGGCCAG ATCTGAGCCTGGGAGCTCTCTGGCC-3' | SEQ. ID. NO: 39 |
| 16S | 5'-CCGTAATACGACTCACTATAGGCGTC ACACCTTCGGGTGAAGTCGCC-3' | SEQ. ID. NO: 40 |
| IRES | 5'-CCGTAATACGACTCACTATAGGGACC GTGCATCATGAGCACAAATCCC-3' | SEQ. ID. NO: 41 |

Experimental Example 1

Measurement of Binding Force to Target RNA Using Alanine Scanned Peptide Library Binding force to each target hairpin RNA (IRES, RRE, TAR and 16S A-site) was measured by fluorescence polarization using alanine scanned peptide library (1b-1h).

Particularly, 100 ml of each target RNA was prepared at the concentration of 10 mM, which stood at 65° C. for 10 minutes and then cooled down slowly at room temperature, leading to folding. The amphiphilic peptide was prepared respectively at the concentration of 100 mM and 1.0 mM, which were maintained at 0° C. As a probe, rev peptide labeled with rhodamine (Rev-N-rhodamine) emitting 200 nM fluorescence was prepared at the concentration of 10 mM. Buffer was composed of 140 mM NaCl, 5 mM KCl, 1 mM MgCl2, and 20 mM HEPES (N-2-Hydroxyethylpiperazine-N'-2-Ethanesulfonic Acid, pH 7.4). Fluorescence Anisotropy was measured using AMINCO-Bowman Series Luminescence Spectrometer at 20° C. Ten nM of the probe was added in 450 mL of buffer, to which target RNA was added to induce interaction between the probe and the target RNA. At that time, anisotropy value increased. Then, the synthesized peptide competing with the probe for binding site was added thereto with increasing the concentration slowly. Changes of fluorescence polarization were measured until fluorescence polarization reached as low as the beginning. Considering the concentration and amount of the peptide added, binding force to target RNA was calculated. That is, the binding strength between target RNA and peptide was determined according to the following Kaleida-Graph.

$$[Peptide] = Kd(A_{max}-A)/[Kd(A-A_0)+1] \times [RNA] - Kd(A-A_0)^2[Probe]_0/(A_{max}-A)(A_{max}-A_0)$$

Herein, [Peptide] indicates the concentration of peptide, [RNA] indicates the concentration of target RNA, and $[Probe]_0$ indicates the concentration of probe. A is the value of fluorescence anisotropy of sample, $A_{max}$ is the value of totally bound tracer, and $A_0$ is the value of totally free tracer.

To investigate alpha-helix of the amphiphilic peptide (1a-1h), circular dichroism (CD) was performed. Particularly, CD was measured at 20° C. by using JASCO model J715 spectropolarimeter. Scanning was performed at 190-250 nm three times (bandwidth: 1 nm, datapitch: 0.5 nm, speed: 100 nm/min), which were averaged to obtain CD data. Spectrum was corrected by measuring background spectrum. CD signal was recorded after modulating thereof with mean residue ellipticity [Q]. Percentage (%) of alpha-helix(fn) was calculated by the following formula.

$$[Q] = Qobs[MRW/(10lc)]$$

MRW=mean residue weight (dividing molecular weight by the number of peptide bond, l=pathway length (cm), c=concentration (mg/mL).

$$fn = ([Q]222 - [Q]coil)/([Q]helix - [Q]coil)$$

$$[Q]helix = -40,000(1-2.5n) + 100t$$

$$[Q]coil = 640 - 45t$$

[Q]222=mean residue ellipticity at 222 nm (deg cm2 mol-1), [Q]helix=ellipticity of peptide having complete helical structure, [Q]coil=ellipticity of peptide having complete random coil structure, n=number of amino acid, t=° C.

As shown in Table 3, binding force of the amphiphilic peptide (1b-1h) to TAR was the weakest and the standard deviation was also very small (70±60 nM). On the contrary, binding force of the peptide to the 16S A-site was the strongest (130±70 nM). In the meantime, standard deviation of binding force of the peptide to IRES was the biggest (100±70 nM). The above results were contrary to that of the original peptide demonstrating the strongest affinity to TAR (66 nM) but weak binding force to IRES hairpin (45 nM). Since TAR is most flexible in morphology, it accepts the amphiphilic peptide flexibly to combine its hairpin and the peptide, indicating increased binding force. Among 7 promiscuous peptides, 4 peptides showed increased binding force to TAR, compared with the original peptide, while only one peptide among those 7 peptides showed increased binding force to IRES, compared with the original peptide. The above results suggest that IRES is a more specific hairpin target. It is believed that the biggest difference observed in IRES binding is owing to the mentioned characteristics of IRES (greater specificity). The amine group which takes an important part of IRES hairpin binding of peptide is located at the sites of #6, #9 and #13. So, when the amine group was removed, binding force was significantly decreased. Therefore, if RNA hairpin specific binding force and deviation of the binding force are investigated by using an alpha scanning peptide library, it can be judged whether the specific hairpin has promiscuous structure or not.

Only peptide 1d demonstrated three fold binding strength to TAR. In the meantime, at least three peptides (1d, 1e, 1g) showed reduced binding strength to IRES. The above results indicate that to be bound with IRES, at least three lysines are essential but to be bound with TAR, lysine does not matter, which is the typical characteristics of a promiscuous hairpin target. Therefore, it can be judged by using an alpha scanning peptide library that which lysine residue plays a crucial role in binding with target hairpin RNA.

TABLE 3

Binding strength and alpha-helical rate of the first generation peptide library prepared by scanning the amphiphilic peptide (1a) with alanine

| No. | SEQ. ID. NO: | Alpha-helical rate (%) | Dissociation constant [nM] (differentiation coefficient) | | | |
|---|---|---|---|---|---|---|
| | | | RRE | TAR | 16S A-site | IRES |
| 1a | 1 | 26/57 | 22 | 66 | 100 | 45 (1.4) |
| 1b | 2 | 9/44 | 140 | 16 | 160 | 53 (2.0) |
| 1c | 3 | 10/42 | 56 | 87 | 92 | 62 (1.3) |
| 1d | 4 | 12/47 | 150 | 150 | 160 | 150 (1.0) |
| 1e | 5 | 12/43 | 130 | 74 | 180 | 120 (1.1) |
| 1f | 6 | 17/45 | 92 | 25 | 64 | 33 (1.8) |
| 1g | 7 | 8/44 | 90 | 39 | 200 | 210 (0.47) |
| 1h | 8 | 9/43 | 25 | 63 | 53 | 49 (0.96) |

Experimental Example 2

Measurement of Binding Strength to Target RNA Using Amphiphilic Peptide Library Having Modification on Hydrophilic Face Lysines at #6, #9 and #13 sites confirmed as important amine group positions by alanine scanning in Experimental Example 1 were substituted with ornithine (Orn), 1,4-diaminobutyric acid (Dab) or 1,3-dipropanoic acid (Dap), amine groups having less carbon number, resulting in the preparation of the second generation peptides. When the amino acid having amine groups linked to shorter residues is used, the outer diameter of a peptide becomes shorter while increasing the chances of being located more deeply in the target RNA groove. In addition, the important amine group remains allowing Van der Waals forces to work more strongly and allowing interaction between the peptide of hydrophobic face and the target RNA to be recognized.

As a result, as shown in Table 4, IRES specific binding strength of the second generation peptides using shorter amino acid was significantly increased, compared with the first generation peptides. Maximum points of such increase were also confirmed by the decrease of carbon number. The binding strength was at least three times that of the peptide using lysine. In the case of the peptide where at least two lysines were substituted with shorter amino acids, binding strength was significantly increased (Kd=680 pM), compared with that of the peptide having modification of only 2m. The peptides were confirmed by alanine scanning as peptides having amine group favorable for binding to IRES, and thus they had very high differentiation coefficient [differentiation coefficient=(mean $K_d$ to other hairpin RNA)/($K_d$ to one hairpin RNA); the higher the differentiation coefficient, the higher the selectivity of peptide is]. Differentiation coefficient for peptide 2k was 24, suggesting that the selectivity was significantly increased, compared with other peptides.

TABLE 4

Binding strength and alpha-helical rate of the second generation peptide library prepared by introducing lysine derivatives with different lengths into hydrophilic face of the amphiphilic peptide

| No. | SEQ. ID. NO: | Alpha-helical rate (%) | Dissociation constant [nM] (differentiation coefficient) | | | |
|---|---|---|---|---|---|---|
| | | | RRE | TAR | 16S A-site | IRES |
| 2a | 9 | 13/82 | 17 | 14 | 15 | 6.1 (2.5) |
| 2b | 10 | 23/63 | 10 | 7.3 | 13 | 1.6 (6.4) |
| 2c | 11 | 26/61 | 9.6 | 5.7 | 12 | 3.8 (2.4) |
| 2d | 12 | 28/57 | 7.6 | 9.8 | 18 | 1.3 (8.7) |
| 2e | 13 | 43/57 | 23 | 28 | 17 | 3.5 (6.5) |
| 2f | 14 | 25/57 | 10 | 11 | 15 | 20 (0.6) |
| 2g | 15 | 36/53 | 11 | 9.0 | 23 | 4.4 (3.3) |
| 2h | 16 | 24/34 | 14 | 12 | 25 | 8.7 (2.0) |
| 2i | 17 | 39/54 | 23 | 8.4 | 20 | 1.4 (12) |
| 2j | 18 | 49/57 | 21 | 10 | 14 | 2.4 (6.3) |
| 2k | 19 | 48/61 | 20 | 13 | 17 | 0.68 (25) |
| 2l | 20 | 40/50 | 14 | 16 | 14 | 1.1 (13) |
| 2m | 21 | 49/69 | 19 | 31 | 13 | 4.3 (4.9) |

Experimental Example 3

Measurement of Binding Strength to Target RNA Using Amphiphilic Peptide Library Having Modification on Hydrophobic Face The hydrophobic region of the amphiphilic peptide can also play a certain role in binding with RNA when the peptide is located deeply in a target RNA groove. So, the hydrophobic region of the amphiphilic peptide was modified and binding strength of the peptide was investigated. It has been well-known that recognition of aliphatic amino acids and RNA do not significantly differ and that aromatic amino acids might have different recognition characteristics. So, the tryptophan scanning peptide library (2n-2u) was constructed by inserting tryptophans in 8 leucine sites on the hydrophobic face, followed by investigation of binding strength to IRES.

As a result, as shown in Table 5, average $K_d$ value to IRES of the tryptophan scanned peptide was 12 nM, which was a four fold increase from the original peptide (1a). This result indicates that the hydrophobic face also plays an important role in RNA recognition of a peptide. So, tryptophan has a site specific effect. In particular, binding strength of 2n, 2q and 2u was significantly increased and binding constant was not even close to nM. In the case of 2n, alpha-helix was significantly increased owing to tryptophan and binding strength to not only IRES but also other hairpins was increased. However, in the case of 2q and 2u, alpha-helix was not much increased by tryptophan substitution but binding strength to IRES was significantly increased. This result indicates that the indole group of tryptophan could increase RNA recognition by specific arrangement with specific nucleotide sequence of RNA. Fluorescence strength of tryptophan of 2u was reduced by 1.6 fold and the wavelength moved to shorter site, suggesting that tryptophan recognized specific nucleotides of IRES. In addition, even if the tryptophan scanned peptide was not a peptide having specific structure, the tryptophan scanned peptide demonstrated high differentiation coefficient to IRES hairpin, indicating that an indole could recognize specifically with RNA nucleotide. In the case of the peptide where two amino acid residues were substituted with indole, binding strength was not much different from the one having only one substitution, supporting the above specific recognition.

TABLE 5

Binding strength and alpha-helical rate of the second generation peptide library prepared by scanning hydrophobic face of the amphiphilic peptide with tryptophan

| No. | SEQ. ID. NO: | Alpha-helical rate (%) | Dissociation constant [nM] (differentiation coefficient) | | | |
|---|---|---|---|---|---|---|
| | | | RRE | TAR | 16S A-site | IRES |
| 2n | 22 | 48/65 | 2.5 | 2.0 | 0.76 | 0.74 (2.4) |
| 2o | 23 | 4.6/52 | 5.9 | 34 | 15 | 3.3 (5.6) |
| 2p | 24 | 20/56 | 6.2 | 9.8 | 12 | 2.8 (3.3) |
| 2q | 25 | 19/71 | 1.2 | 21 | 17 | 0.87 (15) |
| 2r | 26 | 14/59 | 37 | 82 | 65 | 92 (0.75) |
| 2s | 27 | 27/60 | 9.5 | 43 | 24 | 4.4 (5.8) |
| 2t | 28 | 12/58 | 13 | 10 | 17 | 2.3 (5.9) |
| 2u | 29 | 20/52 | 18 | 7.8 | 3.3 | 0.69 (14) |

Experimental Example 4

Measurement of Binding Strength to Target RNA Using Amphiphilic Peptide Library Having Modification on Both Hydrophobic Face and Hydrophilic Face In Experimental Example 2, it was observed that binding strength and selectivity could be changed by substituting hydrophilic lysine with short amino acids in the peptide. In Experimental Example 3, it was also confirmed that binding strength and selectivity to IRES could be changed by substituting hydrophobic leucine with tryptophan in the peptide. So, to investigate what will happen if the said two effective changes occur simultaneously, the present inventors prepared the third generation peptides (3a-3h) having the combination for the said two changes, followed by investigation of the binding strength to IRES hairpin.

As a result, as shown in Table 6, most of the third generation peptides did not demonstrate increased binding strength as expected, but the variation of binding strength showed big differences. Only a few of those third generation peptides demonstrated strong binding strength to IRES hairpin. This result suggests that two changes are dependent each other and when they are complementary, the effect will be maximized. Peptides 3d ($K_d$=0.55 nM) and 3e ($K_d$=0.62 nM) showed the highest binding strength. They had modifications at different sites of the hydrophobic face and hydrophilic face, suggesting that the changes are necessarily dependent on each other.

Fluorescence strength was measured to investigate target RNA binding of the third generation peptides. When tryptophan is activated by 285 nm light, it becomes fluorescent at the wavelength. Changes of fluorescence resulted from the binding respectively to different targets such as IRES, RRE, TAR and 16S A-site RNA, were measured. 0.02 equivalent of target RNA was added slowly to 1 uM peptide solution containing tryptophan. Fluorescence was gradually decreased and at the same time peak point moved to the left gradually, indicating the interaction between the target RNA and the amphiphilic peptide.

Fluorescence strength of tryptophan at #7 of peptide 3d was reduced 2.3 fold from that of tryptophan at #14 of peptide 3h in the presence of IRES, suggesting that the indole group of tryptophan specifically recognizes specific nucleotide of IRES. In the case of the second generation peptides scanned with single tryptophan, fluorescence strength of tryptophan at #14 was reduced most significantly, indicating that a small change on hydrophilic face might result in big changes of hydrophobic face and indole group could recognize specifically the specific IRES nucleotide.

Solid surface method was performed to investigate specificity to target RNA of the third generation peptides. Particularly, biotin was conjugated to N-terminal of the peptide, resulting in the preparation for streptavidin binding. 5'-end of target RNA was labeled with an isotope. Streptavidin coated plate was prepared, to which the amphiphilic peptide was adhered at different concentrations. The plate was reacted with a certain amount of the isotope-labeled RNA, followed by washing. Only the RNA conjugated with the amphiphilic peptide was obtained. $IC_{50}$ was calculated based on the concentration of the target RNA. Experiments were performed in the presence and in the absence of tRNA$^{mix}$ (Sigma-Aldrich, Germany), and the results were compared. That is, peptides having higher target RNA binding strength shows higher differentiation rate, compared with the general RNA, tRNA, by which specificity of the amphiphilic peptide was confirmed.

Figure 3:
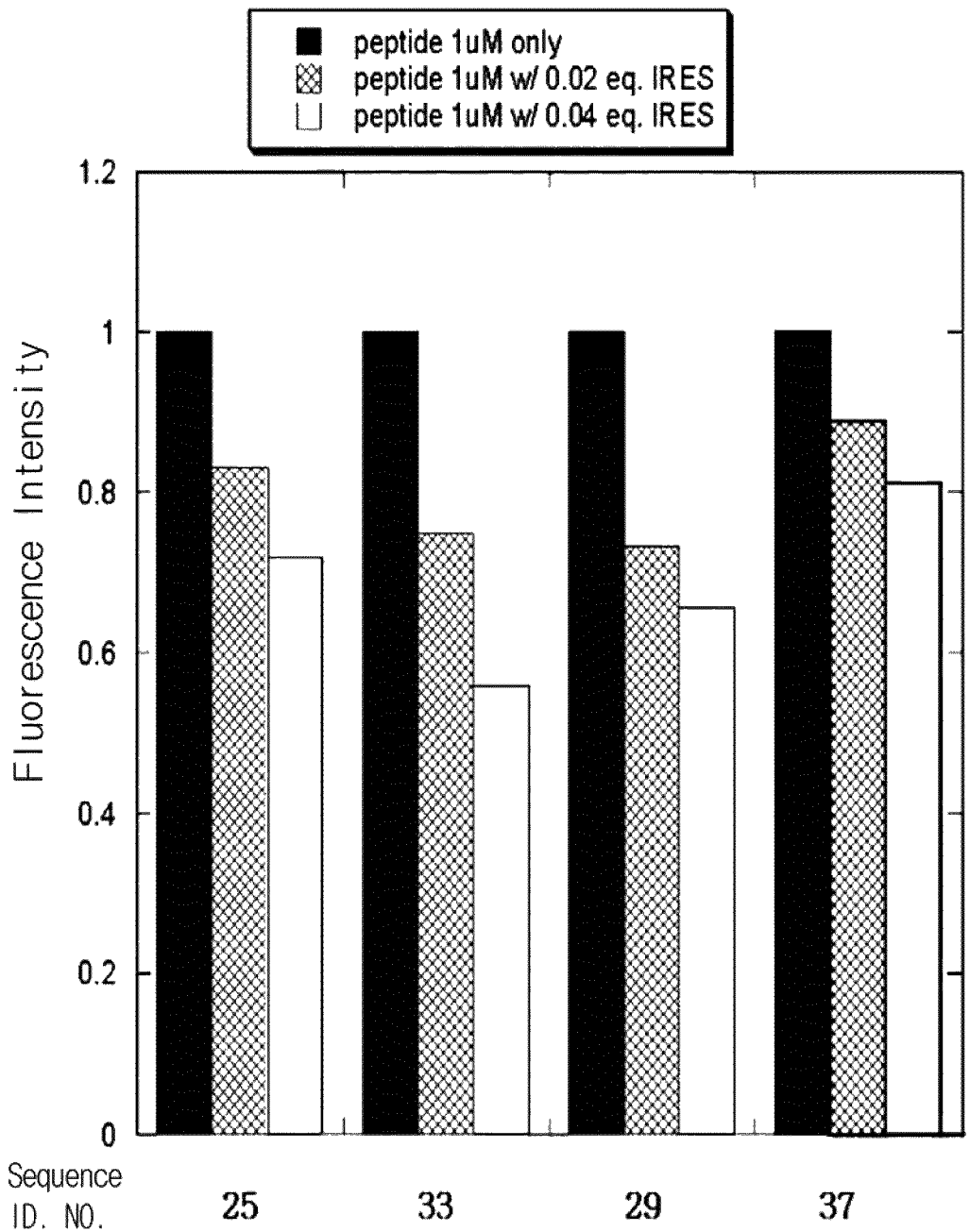
FIG. 3 is a graph illustrating the fluorescent strength to IRES RNA of the peptide library of the present invention.
Figure 4:
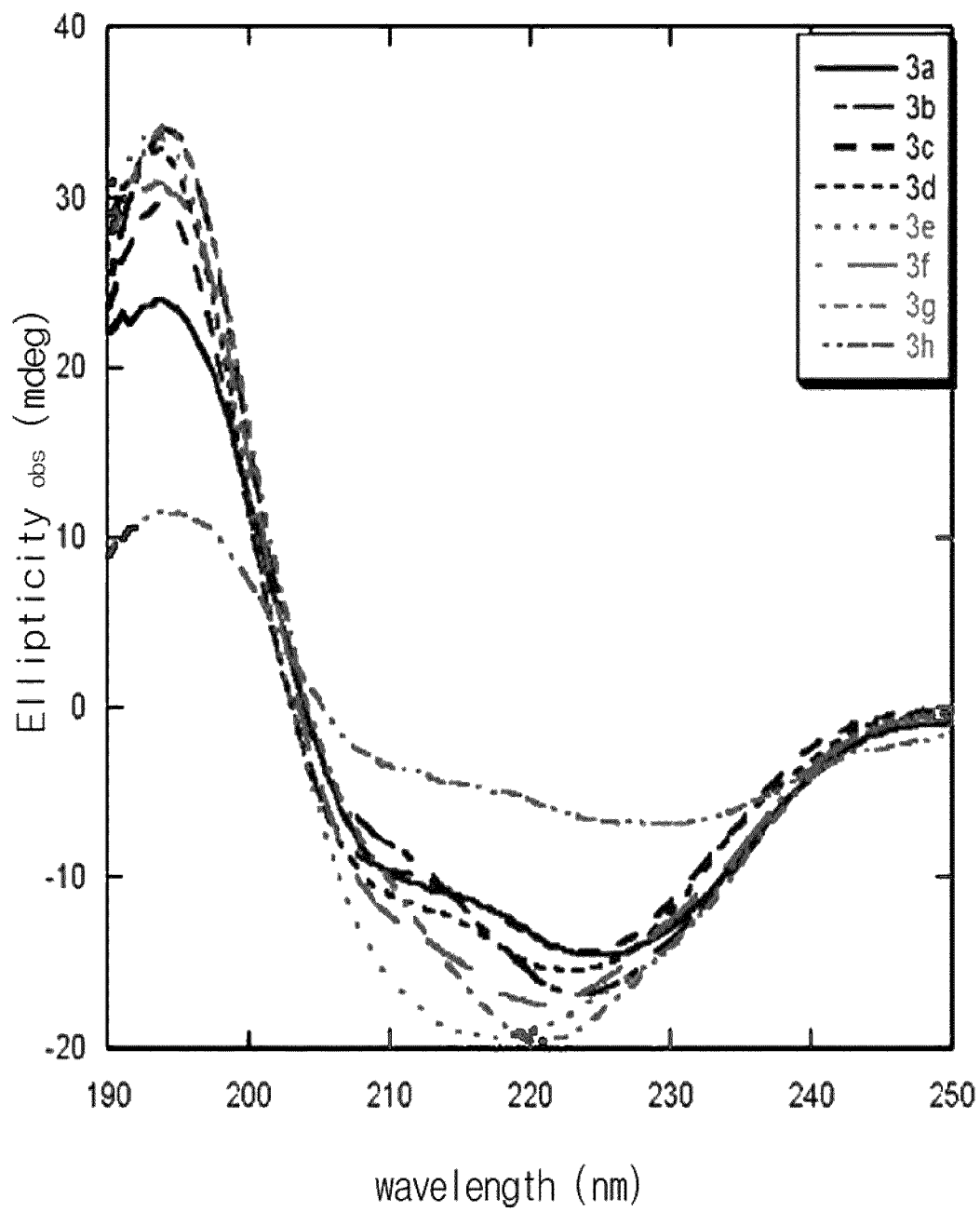
FIG. 4 is a graph illustrating the result of measurement of CD to IRES RNA of the peptide library of the present invention.
Figure 5:
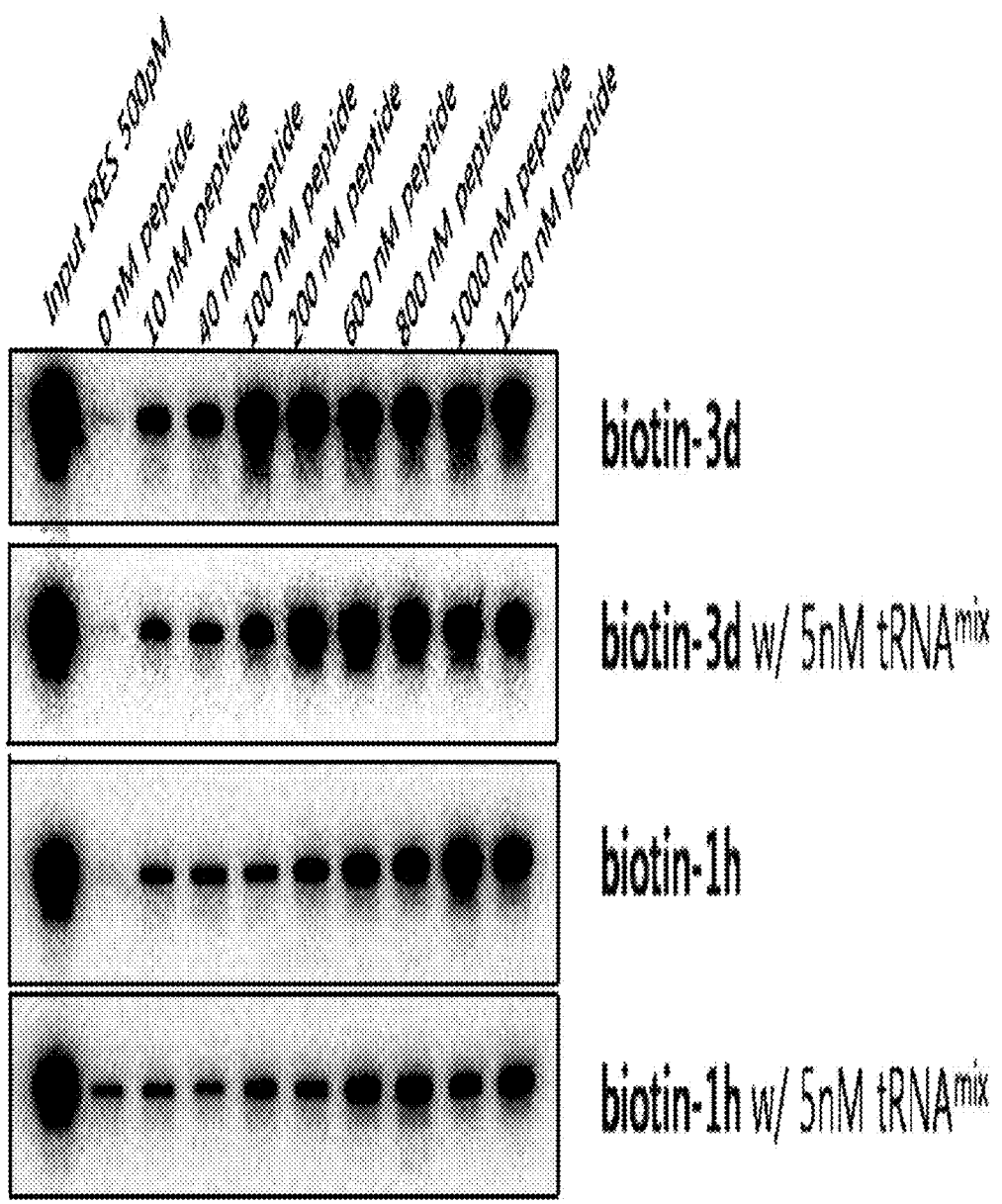
FIG. 5 is a graph illustrating the result of measurement of binding force to IRES RNA of the peptide library of the present invention via solid surface method.

$IC_{50}$ to IRES RNA of 3d peptide was investigated in the presence or in the absence of tRNA$^{mix}$. As a result, binding strength was not much different (FIG. 3), suggesting that the peptide has IRES specific recognition which is selective and specific.

TABLE 6

Binding strength and alpha-helical rate of the third generation peptide library prepared by modification of hydrophilic face and hydrophobic face of the amphiphilic peptide

| No. | SEQ. ID. NO: | Alpha-helical rate (%) | Dissociation constant [nM] (differentiation coefficient) | | | |
|---|---|---|---|---|---|---|
| | | | RRE | TAR | 16S A-site | IRES |
| 3a | 30 | 29/55 | 22 | 19 | 13 | 1.8 (10) |
| 3b | 31 | 34/52 | 18 | 22 | 24 | 5.1 (4.2) |
| 3c | 32 | 29/36 | 9.7 | 8.3 | 21 | 0.75 (17) |
| 3d | 33 | 32/38 | 26 | 24 | 25 | 0.55 (45) |
| 3e | 34 | 39/45 | 22 | 14 | 16 | 0.62 (28) |
| 3f | 35 | 36/58 | 3.6 | 4.7 | 10 | 6.1 (1.0) |
| 3g | 36 | 41/63 | 11 | 5.9 | 17 | 1.2 (9.4) |
| 3h | 37 | 12/56 | 28 | 15 | 19 | 13 (1.6) |

Figure 2:
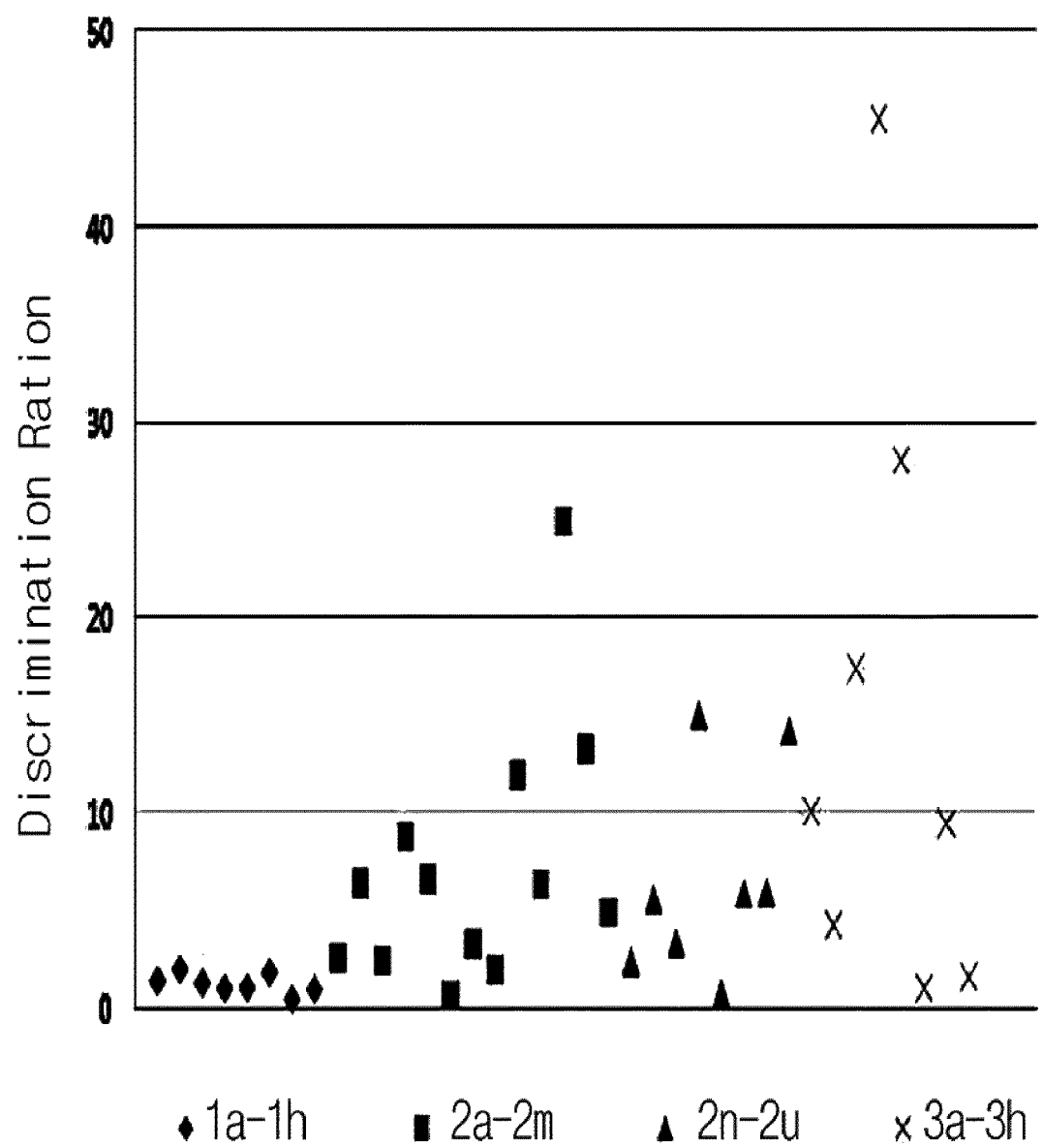
FIG. 2 is a graph illustrating the differentiation coefficient to IRES RNA of the first, the second and the third generation peptide libraries of the present invention.

Peptides having modifications on both hydrophilic face and hydrophobic face and have strong binding strength to IRES were not many, but their peptide differentiation coefficient was high (FIG. 2). Such high differentiation coefficients indicate that the amphiphilic peptide needs the participation of both the hydrophilic face and hydrophobic face for being a selective and specific ligand to RNA hairpins. That is, the differentiation coefficient of the second generation peptides was about 20. But, the differentiation coefficient of the third generation peptides was at least 40, which was about 2.3 fold increased value from that of the second generation peptides. The binding strength was increased only 1.2 times, but selectivity was relatively increased significantly.

INDUSTRIAL APPLICABILITY

The amphiphilic peptides having specificity and strong binding strength to hairpin RNA selected in the invention can be effectively used for the study of hairpin RNA functions or for the production of a novel drug using an artificial peptide to bind to a hairpin RNA target.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

One of ordinary skill in the art will appreciate that starting materials, reagents, purification methods, materials, substrates, device elements, analytical methods, assay methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A method of screening an amphiphilic peptide binding specifically to a target hairpin RNA for production of a diagnostic reagent for hepatitis C virus comprising the steps of:
   1) constructing an amphiphilic peptide library containing the amphiphilic peptide consisting of the amino acid sequences of SEQ. ID. NO: 1-No: 37;
   2) synthesizing Internal Ribosome Entry Site (IRES) RNA as the target hairpin RNA of hepatitis C virus;
   3) calculating binding force between RNA and the amphiphilic peptide by measuring fluorescent anisotropy of a mixture composed of the amphiphilic peptide, hairpin RNA and a fluorescent compound by using a fluoro spectrophotometer; and
   4) selecting the amphiphilic peptide, wherein said amphiphilic peptide has a dissociation constant less than 4.3 nM or a differentiation coefficient more than 4.9.

2. The method of screening according to claim 1, wherein the compound is rhodamine conjugated rev peptide (Rev-N-rhodamine).

3. The method of screening according to claim 1, wherein the selection of step 4) comprises selecting the amphiphilic peptide, wherein said amphiphilic peptide has a dissociation constant less than 0.87 nM or a differentiation coefficient more than 14.

4. The method of screening according to claim 1, wherein the selection of step 4) comprises selecting the amphiphilic peptide, wherein said amphiphilic peptide has a dissociation constant less than 0.62 nM or a differentiation coefficient more than 28.

* * * * *